(12) United States Patent
Yee et al.

(10) Patent No.: US 10,502,756 B2
(45) Date of Patent: Dec. 10, 2019

(54) FLEXIBLE MICROFLUIDIC MOTION SENSORS

(71) Applicant: Robert Bosch GmbH, Stuttgart (DE)

(72) Inventors: Seow Yuen Yee, Mountain View, CA (US); Ashwin Samarao, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 80 days.

(21) Appl. No.: 15/686,387

(22) Filed: Aug. 25, 2017

(65) Prior Publication Data

US 2018/0059134 A1    Mar. 1, 2018

Related U.S. Application Data

(60) Provisional application No. 62/379,915, filed on Aug. 26, 2016.

(51) Int. Cl.
*G01P 15/00* (2006.01)
*A61B 5/11* (2006.01)
(Continued)

(52) U.S. Cl.
CPC .......... *G01P 15/006* (2013.01); *A61B 5/1126* (2013.01); *B01L 3/505* (2013.01); *B01L 3/502715* (2013.01); *B01L 3/502784* (2013.01); *G01C 9/06* (2013.01); *G01C 9/24* (2013.01); *G01C 19/58* (2013.01); *G01N 27/07* (2013.01); *G01P 13/00* (2013.01); *A61B 2562/028* (2013.01); *A61B 2562/168* (2013.01); *B01L 2200/0673* (2013.01);
(Continued)

(58) Field of Classification Search
CPC .... G01P 15/006; G01C 9/26; A61B 2562/168

USPC .......................... 73/514.09, 504.07, 514.03
See application file for complete search history.

(56) References Cited

U.S. PATENT DOCUMENTS

| | | | |
|---|---|---|---|
| 2009/0139329 A1* | 6/2009 | Shinogi ................. | G01P 15/006 73/514.09 |
| 2009/0158605 A1* | 6/2009 | Montgomery ........... | G01C 9/26 33/379 |
| 2016/0025535 A1 | 1/2016 | Byers et al. | |

OTHER PUBLICATIONS

International Search Report corresponding to International Patent Application No. PCT/EP2017/071495 (4 pages).

(Continued)

*Primary Examiner* — John E Chapman, Jr.
(74) *Attorney, Agent, or Firm* — Maginot, Moore & Beck LLP

(57) ABSTRACT

A flexible electronic device includes a flexible electronic circuit and a flexible microfluidic sensor homogeneously integrated into the flexible circuit. The flexible sensor includes a flexible microfluidic structure, a first material, a second material, and an electrode arrangement. At least one of the first and second materials is a fluid. The structure defines at least one microfluidic chamber. The first and second materials are disposed in the chamber. The second material has a physical property and an electrical property different from the first material. The electrode arrangement includes at least one pair of electrodes spaced apart from each other with at least a portion of the at least one chamber located functionally directly therebetween such that at least one electronic property measured across the pair is based on a relationship between the second material and the electrode pair. The relationship is based on a physical condition of the microfluidic structure.

20 Claims, 5 Drawing Sheets

(51) Int. Cl.
*G01P 13/00* (2006.01)
*B01L 3/00* (2006.01)
*G01N 27/07* (2006.01)
*G01C 9/06* (2006.01)
*G01C 9/24* (2006.01)
*G01C 19/58* (2006.01)
*G01C 9/10* (2006.01)

(52) U.S. Cl.
CPC .................. *B01L 2300/0645* (2013.01); *B01L 2300/0663* (2013.01); *B01L 2300/0672* (2013.01); *G01C 2009/107* (2013.01)

(56) References Cited

OTHER PUBLICATIONS

Focke, Maximilian et al., "Lab-on-a-Foil: mircofluidics on thin and flexible films," The Royal Society of Chemistry, pp. 1365-1386, 2010 (22 pages).

* cited by examiner

FLEXIBLE MICROFLUIDIC MOTION SENSORS

RELATED APPLICATIONS

This Application claims the benefit of priority to U.S. Provisional Application No. 62/379,915 entitled "Flexible Microfluidic Motion Sensors" filed on Aug. 26, 2016, the disclosure of which is incorporated herein in its entirety.

TECHNICAL FIELD

This disclosure relates generally to flexible sensors and, more particularly, to flexible microfluidic motion sensors.

BACKGROUND

Continuing development toward wearable devices and the internet-of-things has motivated the development of flexible electronics. Customarily, electronics were formed on rigid silicon platforms that were not well adapted to these uses. To address this issue, flexible electronics have been developed that are formed on flexible polymer-based platforms. One difficulty encountered with the use of flexible polymer-based platforms is the integration of motion sensors.

Motion sensors, including accelerometers and gyroscopes, are used in a wide variety of applications, and generally include a structure formed onto a silicon platform. As a result, current solutions provide a heterogeneous integration of silicon-based sensors with polymer-based electronics. The silicon sensors decrease the flexibility of the resulting device, and flexure of the device can negatively impact the performance of the sensors. Additionally, since the sensors and electronics are made using different platforms, manufacturing such heterogeneous devices becomes increasingly complex, costly, and time-consuming.

Based on the foregoing, a motion sensor that is flexible would be beneficial. A motion sensor that can be formed homogeneously with flexible electronics would also be beneficial.

SUMMARY

A flexible microfluidic sensor according to this disclosure includes a flexible microfluidic structure, a first material, a second material, and an electrode arrangement. The structure defines at least one microfluidic chamber. The first and second materials are disposed in the chamber. The second material has a physical property and an electrical property different from the first material. The electrode arrangement includes at least one pair of electrodes spaced apart from each other with at least a portion of the at least one chamber located functionally directly therebetween such that at least one electronic property measured across the pair is based on a relationship between the second material and the at least one electrode pair. The relationship between is based on a physical condition of the microfluidic structure.

In some embodiments, the physical condition of the microfluidic structure includes at least one of an orientation of the microfluidic structure, an acceleration of the microfluidic structure, and a rotation rate of the microfluidic structure.

In some embodiments, the first material is a first fluid. In some embodiments, the first fluid includes at least one of a liquid and a gas.

In some embodiments, the second material is a second fluid. In some embodiments, the second fluid includes at least one of a liquid and a gas.

In some embodiments, the second material includes a solid. In some embodiments, the second material consists of a solid. In some embodiments, the second material includes a fluid disposed within a solid shell.

In some embodiments, the at least one physical property includes at least one of density and viscosity.

In some embodiments, the at least one electrical property measured across the at least one pair of electrodes includes at least one of resistance and capacitance.

In some embodiments, the at least one chamber includes a first microfluidic channel that extends along a first axis. The second fluid forms a first bubble within the first fluid in the first microfluidic channel. The at least one pair of electrodes includes a first set of electrode pairs distributed along the first axis of the first microfluidic channel such that at least one electronic property measured across the first set of electrode pairs is based on a relationship between the first bubble and the first set of electrode pairs. The relationship between the first bubble and the first set of electrode pairs is based on at least one of an orientation of the first axis relative to a direction of gravity, an acceleration of the microfluidic structure along the first axis, and a rotation of the microfluidic structure perpendicular to the first axis.

In some embodiments, the relationship between the first bubble and the first set of electrode pairs includes at least one of a location of the first bubble along the first axis and a diameter of the first bubble.

In some embodiments, each electrode in the first set of electrode pairs includes a respective electrical contact.

In some embodiments, the sensor includes a measurement device electrically connected to the electrical contacts of the electrodes in the first set of electrode pairs. The measurement device is configured to determine the relationship between the first bubble and the first set of electrode pairs based on the at least one electrical property measured across the first set of electrode pairs distributed along the first axis, and to determine, based on the determined relationship, a physical condition of the microfluidic structure.

In some embodiments, each electrode pair in the first set of electrode pairs has a respective resistive load so that the resistive load of the first set of electrode pairs varies along the first axis. The at least one electrical property measured across the first set of electrode pairs includes resistance, such that a total resistance of the first set of electrode pairs changes based on the location of the first bubble along the first microfluidic channel. The measurement device is further configured to determine the location of the first bubble along the first microfluidic channel based on the total resistance of the first set of electrode pairs.

In some embodiments, the at least one chamber includes a second microfluidic channel that extends along a second axis extending perpendicularly to the first axis. The second fluid forms a second bubble within the first fluid in the second microfluidic channel. The at least one pair of electrodes includes a second set of electrode pairs distributed along the second axis of the second microfluidic channel such that at least one electronic property measured across the second set of electrode pairs is based on a relationship between the second bubble and the second set of electrode pairs. The relationship between the second bubble and the second set of electrode pairs is based on at least one of an orientation of the second axis relative to the direction of gravity, an acceleration of the microfluidic structure along the second axis, and a rotation of the microfluidic structure perpendicular to the second axis.

In some embodiments, the at least one chamber includes a third microfluidic channel that extends along a third axis extending perpendicularly to the first axis and perpendicularly to the second axis. The second fluid forms a third bubble within the first fluid in the third microfluidic channel. The at least one pair of electrodes includes a third set of electrode pairs distributed along the third axis of the second microfluidic channel such that at least one electronic property measured across the third set of electrode pairs is based on a relationship between the third bubble and the third set of electrode pairs. The relationship between the third bubble and the third set of electrode pairs is based on at least one of an orientation of the third axis relative to the direction of gravity, an acceleration of the microfluidic structure along the third axis, and a rotation of the microfluidic structure perpendicular to the third axis.

In some embodiments, the at least one chamber includes a microfluidic cavity that extends along a first axis and along a second axis perpendicular to the first axis. The second fluid forms a bubble within the first fluid in the microfluidic cavity. The at least one electronic property measured across the at least one pair of electrodes is based on a relationship between the bubble and the at least one pair of electrodes. The physical condition of the microfluidic structure includes at least one of an acceleration of the microfluidic structure along the first axis, an acceleration of the microfluidic structure along the second axis, an orientation of the second axis relative to a direction of gravity, an orientation of the first axis relative to the direction of gravity, and a rotation of the microfluidic structure about a third axis perpendicular to the first axis and the second axis.

In some embodiments, the microfluidic cavity has a first diameter, and is configured to flex due to rotation of the microfluidic structure about the third axis such that the first diameter increases. The at least one bubble has a second diameter that is based on the first diameter, such that the second diameter is based on the rotation of the microfluidic structure about the third axis.

In some embodiments, the at least one electronic property measured across the at least one pair of electrodes includes capacitance. The at least one electronic property of the second fluid includes dielectric permittivity such that the capacitance measured across at least one electrode pair changes based on the second diameter of the at least one bubble.

In some embodiments, the sensor includes a measurement device electrically connected to the at least one electrode pair and configured to determine the rotation rate of the microfluidic structure based on the capacitance measured across the at least one electrode pair.

In some embodiments, the microfluidic structure consists of flexible polymer material.

In some embodiments, the flexible polymer material includes at least one of poly-dimethyle-siloxane and poly (p-xylylene).

A flexible electronic device according to this disclosure includes at least one flexible electronic circuit, and a flexible microfluidic sensor homogeneously integrated with the at least one flexible electronic circuit. The flexible microfluidic sensor includes a flexible microfluidic structure, a first material, a second material, and an electrode arrangement. The structure defines at least one microfluidic chamber. The first and second materials are disposed in the chamber. The first material is a first fluid. The second material is a second fluid, and has a physical property and an electrical property different from the first fluid. The electrode arrangement includes at least one pair of electrodes spaced apart from each other with at least a portion of the at least one chamber located functionally directly therebetween such that at least one electronic property measured across the pair is based on a relationship between the second fluid and pair. The relationship between is based on a physical condition of the microfluidic structure.

In some embodiments, the physical condition of the microfluidic structure is indicative of at least one of an orientation, an acceleration, and a rotation rate of at least a portion of a human user.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one of ordinary skill in the art to which this document pertains.

Figure 1A:
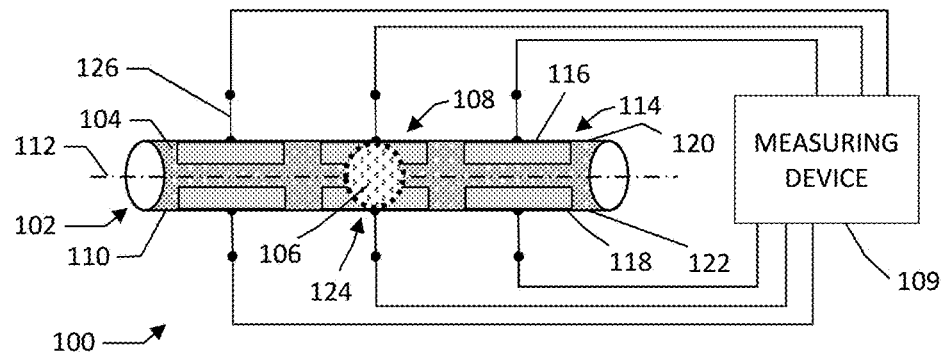
FIG. 1a is a top plan view of an exemplary embodiment of a flexible microfluidic sensor according to this disclosure.
Figure 1B:
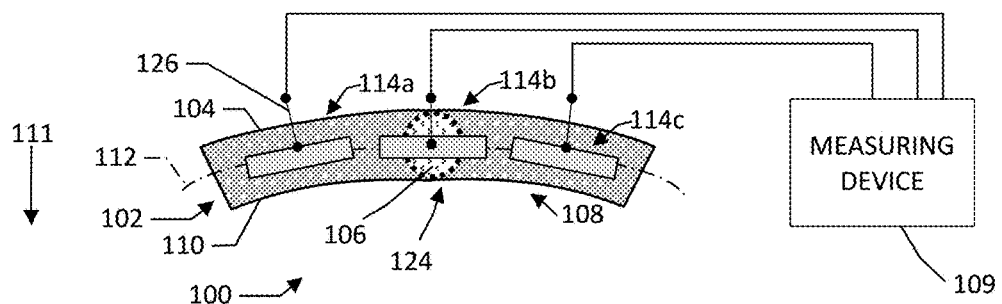
FIG. 1b is a side plan view of the sensor from FIG. 1a in a first orientation.

FIG. 1a depicts a top plan view of an exemplary embodiment of a flexible microfluidic sensor 100 according to this disclosure, and FIG. 1b depicts a side plan view of the sensor 100. The sensor 100 includes a microfluidic structure 102, a first material 104, a second material 106, an electrode arrangement 108, and a measurement device 109.

The microfluidic structure 102 defines a microfluidic chamber 110. In this embodiment, the microfluidic chamber 110 is a microfluidic channel 110 that extends along a first axis 112. As depicted in FIG. 1b, in this embodiment the first axis 112 is curved relative to a direction of gravity 111, and thus the microfluidic channel 110 has a curved shape when viewed from the side. In other embodiments, the axis 112 and microfluidic channel 110 have other shapes.

The microfluidic channel 110 is formed from a flexible material. In one example, the flexible material is a polymer, such as poly-dimethyle-siloxane, poly(p-xylylene), or derivatives or combinations thereof. In this embodiment, the microfluidic channel 110 is closed. In other embodiments, the microfluidic channel is at least partially open. In some embodiments, a membrane at least partially covers an opening in the microfluidic channel.

Generally, at least one of the first material 104 and the second material 106 is a fluid. As used herein, a "fluid" means a material having the capability to flow, and can include a liquid, a gas, a collection of flowable solid particles, or combinations thereof. In this embodiment, the first material 104 is a first fluid, and the second material 106 is a second fluid. In other embodiments, other materials or combinations of materials are used. The first fluid 104 and second fluid 106 are disposed within the microfluidic channel 110. The second fluid 106 has at least one physical property that is different than a physical property of the first fluid 104, and at least one electronic property that is different than an electronic property of the first fluid 104. Specifically, in this embodiment, the first fluid 104 and second fluid 106 have different densities and different resistances. Fluids of different densities will gradually stratify into separate regions arranged in order of increasing density relative to a direction of gravity. More dense materials, having more mass per unit volume, also experience more inertia relative to less dense materials due to, for example, an acceleration or rotation.

In this embodiment, the first fluid 104 has a higher density than the second fluid 106. In other embodiments, the first fluid 104 has a lower density than the second fluid 106. Due to the difference in density, the second fluid 106 forms a bubble 124 within the first fluid 104. As used herein, the term "bubble" means a globule of material that is at least substantially unmixed with other surrounding material.

The first fluid 104 and second fluid 106 can include any acceptable material or combination of materials. In some embodiments, the first fluid 104 and second fluid 106 are liquids. In some embodiments, at least one of the first fluid 104 and second fluid 106 is a gas.

The electrode arrangement 108, in this embodiment, includes a set of electrode pairs 114 distributed along the first axis 112. In this embodiment, the first set 114 includes three pairs 114a-c, but other numbers of pairs are included in other embodiments. For example, some embodiments include only a single pair, while other embodiments include ten, one hundred, or one thousand pairs, or more.

Each electrode pair 114a-c respectively includes electrodes 116 and 118 that are spaced apart from each other with at least a portion of the channel 110 located functionally directly therebetween. As used herein, the phrase "functionally directly therebetween" means "located so as to have an influence on the operation or interaction thereof." In other words, the electrodes 116 and 118 in each pair 114a-c are configured to interact with each other through the at least portion of the microfluidic channel 110 such that the interaction is influenced by the portion of the channel 110 therebetween. In this embodiment, with the first fluid 104 and second fluid 106 having different resistances, the interaction between the electrodes 116 and 118 includes an electronic circuit connection between the electrodes 116 and 118 based on a resistance of the at least portion of the channel 110 functionally directly therebetween. Other types of interactions are also contemplated in other embodiments.

The electrodes 116 and 118 in each electrode pair can include any acceptable material or combination of materials. In this embodiment, the electrodes 116 and 118 in each pair 114 are respectively disposed on opposite sides 120 and 122 of the first microfluidic channel 110. Other location for the electrodes 116 and 118 are also contemplated in other embodiments.

Each pair 114a-c enables the detection of a presence of the bubble 124 in a region near that pair due to the difference in resistance in the first fluid 104 and second fluid 106. In other words, due to the difference in resistance between the first fluid 104 and second fluid 106, the resistance measured across the electrodes 116 and 118 in each pair is different depending on whether the bubble 124 or the first fluid 104 is located functionally therebetween, and that difference is indicative of the presence of the bubble 124.

Each of the electrodes 116 and 118 includes a respective electrical contact 126 connected with the measurement device 109. In this embodiment, the electrical contacts 126 are connected via separate connections with the measurement device 109. In other embodiments, other connection types are also contemplated, such as all of the contacts being connected to the measuring device 109 in parallel.

The measuring device 109 is configured to determine a relationship between the second fluid 106 and the electrode arrangement 108, in this embodiment a location of the bubble 124 along the first axis 112, and is further configured to determine a physical condition of the microfluidic structure based on the determined location. As used herein a "physical condition" means at least one of an orientation relative to a direction of gravity, an acceleration along one or more axes, and a rotation about one or more axes.

The measuring device 109 is configured to determine location of the bubble 124 based on the difference in the interactions of the electrode pairs 114. Specifically, in this embodiment, the measuring device 109 is configured to determine a location of the bubble 124 based on resistances measured across the electrode pairs 114a-c. In FIG. 1b, the bubble 124 is proximate to the pair 114b. Thus, the resistance measured across pair 114b is based on the resistance of the second fluid 106, while the resistance measured across the pairs 114a and 114c is based on the resistance of the first fluid 104. Based on the foregoing, the measuring device 109 is configured to determine that the bubble 104 is located proximate to the pair 114b.

The determined location of the bubble 124 enables the measuring device 109 to determine the physical condition of the microfluidic structure 102 because the difference in physical properties between the first fluid 104 and second fluid 106 cause the first fluid 104 and second fluid 106 respond differently to the physical condition of the microfluidic structure 102, and in particular to the orientation of the firs axis 112 of the microfluidic structure 102 relative to the direction of gravity 111.

Figure 1C:
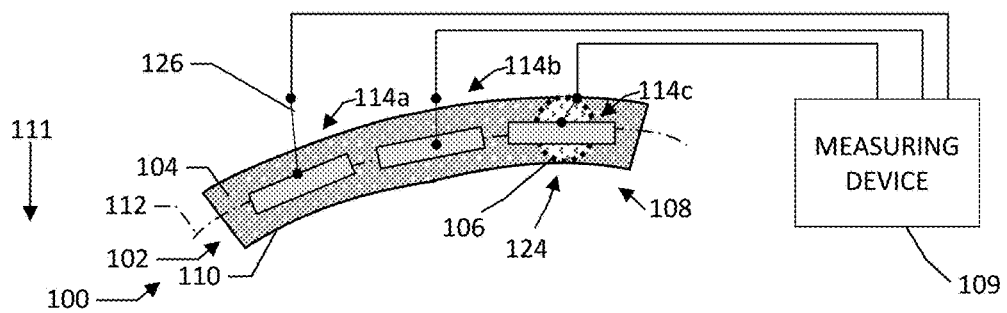
FIG. 1c is a side plan view of the sensor from FIG. 1a in a second orientation.

Specifically, since the second fluid 106 is less dense than the first fluid 104, the bubble 124 is located at a highest point in the microfluidic channel 110 relative to gravity 111. In FIG. 1b, the highest point relative to gravity 111 is proximate to the pair 114b. In FIG. 1c, the microfluidic structure 102 has been reoriented so that the axis 112 is at an angle relative to gravity 111. In FIG. 1c, the highest point relative to gravity 111 is proximate to the pair 114c, and thus the bubble 124 has been relocated along the first axis 112 so as to be proximate to the pair 114c. In other words, a relationship between the second fluid 106 and the electrode pairs 114 is based on the physical condition of the microfluidic structure 102, and moreover is detectable via the measuring device 109 due to the difference in resistance between the first fluid 104 and second fluid 106.

In another embodiment of a flexible microfluidic sensor according to this disclosure, the sensor is structured similarly to the sensor 100 depicted in FIGS. 1a and 1b. In this embodiment, the second fluid 106 has a higher dielectric permittivity than the first fluid 104. A capacitance measured across two electrodes separated by a gap increases with an increased dielectric permittivity in the space therebetween. Thus, in this embodiment, the measurement device 109 is configured to determine the location of the bubble 124 based on capacitances measured across the electrode pairs 114a-c.

In another embodiment of a flexible microfluidic sensor according to this disclosure, the sensor is structured similarly to the sensor 100 depicted in FIGS. 1a and 1b. In this embodiment, the second material is a solid ball. In some embodiments, the solid ball 106 consists of solid material. In other embodiments, the solid ball includes a solid shell filled with fluidic material. The solid shell enables the selection of fluids having desirable physical properties that would otherwise mix or be incompatible with the first fluid. The solid ball behaves similarly to a bubble within the first fluid with regard to the interactions across electrodes and with movement along the microfluidic channel.

In another embodiment of a flexible microfluidic sensor according to this disclosure, the sensor is structured similarly to the sensor 100 depicted in FIGS. 1a and 1b. In this embodiment, the first material is a porous solid material. In some embodiments, the first material is a contiguous material. In some embodiments, the first material includes discrete grains. The second material is a fluid that is able to flow within the porous first material and form a collection within the first material that behaves similarly to a bubble.

Figure 2A:
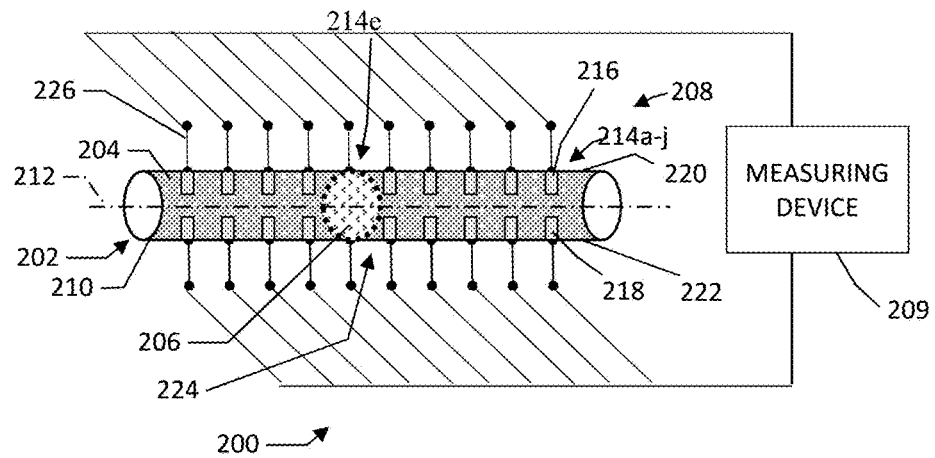
FIG. 2a is a top plan view of another exemplary embodiment of a flexible microfluidic sensor according to this disclosure.

FIG. 2a depicts a top plan view of another exemplary embodiment of a flexible microfluidic sensor 200 according to this disclosure. The sensor 200 includes a microfluidic structure 202 that includes a channel 210, a first fluid 204, a second fluid 206, an electrode arrangement 208, and a measurement device 209. The second fluid 206 has a different resistance and a different viscosity than the first fluid 204. Specifically, in this embodiment, the second fluid has a lower resistance and a lower viscosity than the first fluid 204. The second fluid 206 forms a bubble 224 within the first fluid 204.

The electrode arrangement 208 includes a set of ten electrode pairs 214a-j that each includes electrodes 216 and 218 disposed on diametrically opposed sides 220 and 222 of the microfluidic channel 210. In this embodiment, each of the electronic contacts 226 for the pairs 214a-j is connected to the measurement device 209 in parallel. Further, in this embodiment, each of the pairs 214a-j has a respective resistive load such that the resistive load of the pairs 214a-j varies along the first axis 212. Due to the variance in the resistive loads, and to the difference in resistance between the first fluid 204 and second fluid 206, a total resistance of the electrode pairs 214a-j varies based on a location of the bubble 224 along the first axis 212.

The first fluid 204 acts like an open circuit connection when located functionally directly between an electrode pair due to its relatively high resistance. Conversely, the second fluid 206 acts like a closed circuit connected when located functionally directly between an electrode pair due to its relatively low resistance. As a result, the total resistance of the pairs 114a-j is substantially based on the resistive load of the pair 214e proximate to the bubble 224. The measurement device 209 is thus able to determine the location of the bubble 224 based on the total resistance of the pairs 214a-j, which in FIG. 2a is proximate to the pair 214-e.

Figure 2B:
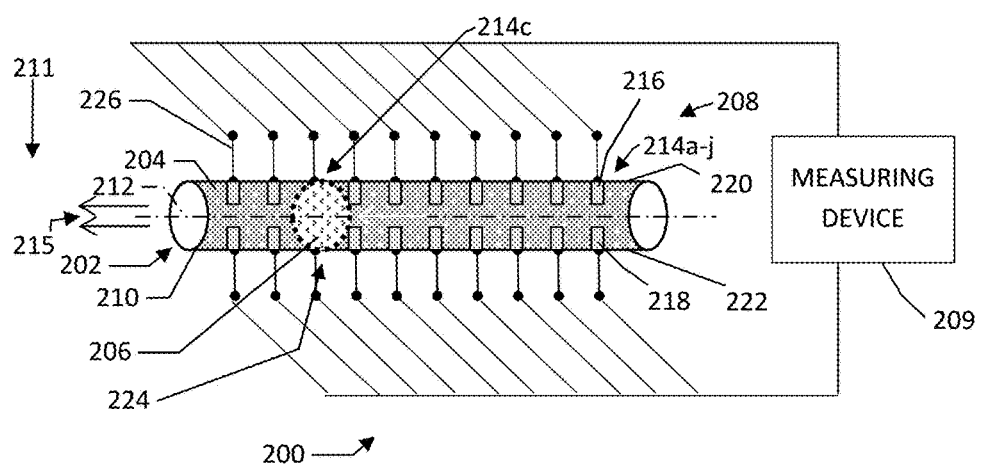
FIG. 2b is a top plan view of the sensor from FIG. 2a subject to an acceleration.

Due to the difference in viscosity, the first fluid 204 and second fluid 206 respond differently to an acceleration of the microfluidic structure 202. In FIG. 2b, the microfluidic structure 202 has been accelerated in a direction 215 substantially along the first axis 212. Since the first fluid 204 has a higher viscosity than the second fluid 206, the first fluid 204 is more resistant to flow, and is thus more resistant to forces caused by the acceleration. As a result, at least a portion of the first fluid 204 moves relative to the bubble 224 counter to the direction 215 of the acceleration, such that the bubble 224 is moved along the first axis 215 in the direction of the acceleration 215. The magnitude of the movement of the bubble corresponds to the magnitude of the acceleration.

In FIG. 2b, the bubble has been moved so as to be proximate to the pair 214c. Thus, as a result of the movement of the bubble 224, the total resistance of the pairs 114a-j in FIG. 2b is substantially based on the resistive load of the pair 214c instead of the pair 241e as in FIG. 2a. The measurement device 209 is configured to determine a magnitude of the motion of the bubble 224 along the first axis 212, and is further configured to determine a physical condition of the microfluidic structure 202 based on the determined magnitude. To determine the magnitude, the measuring device 209 is configured to determine that the location of the bubble 224 has changed, and compare an initial location of the bubble 224 with the new changed location.

In another embodiment of a flexible microfluidic sensor according to this disclosure, the sensor has a similar configuration to the sensor 200 depicted in FIGS. 2a and 2b. In this embodiment, the second fluid 206 has a lower density that the first fluid 204. Due to the difference in density, the second fluid 206 has less inertia than the first fluid 204, which causes the first fluid 204 and second fluid 206 to respond differently to an acceleration of the microfluidic structure 202. In particular, the bubble 224 of the second fluid 206 is less resistant to motion than the first fluid 204, and thus at least a portion of the first fluid moves past the bubble 224 in a direction opposite the acceleration 215 so that the bubble 224 moves along the first axis 212 in the direction of the acceleration.

Figure 3:
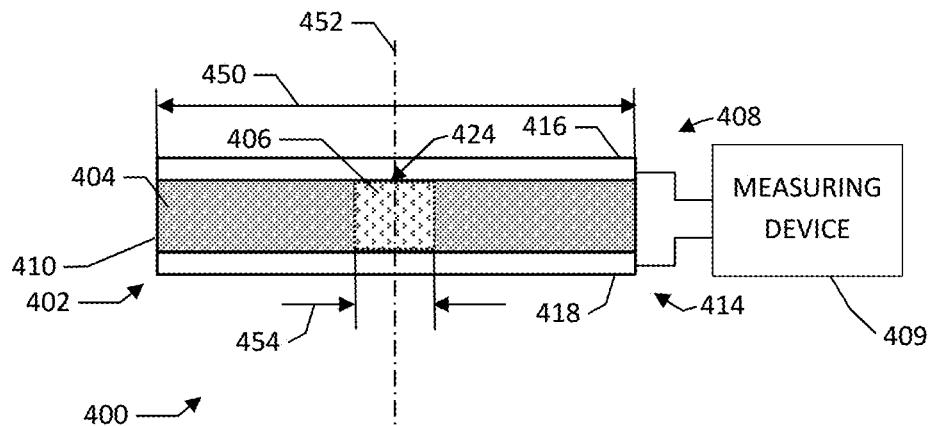
FIG. 3 is a side plan view of another exemplary embodiment of a flexible microfluidic sensor according to this disclosure.

FIG. 3 depicts a side plan view of another exemplary embodiment of a flexible microfluidic sensor 400 according to this disclosure. The sensor 400 includes a flexible microfluidic structure 402, a first fluid 404 and second fluid 406 disposed within the microfluidic structure 402, an electrode arrangement 408, and a measurement device 409.

The microfluidic structure 402 defines a microfluidic chamber that, in this embodiment, includes a microfluidic cavity 410 having a first diameter 450. The microfluidic cavity 410 is configured to flex based on a rotation rate of the microfluidic structure 402 about a rotation axis 452 perpendicular to the first diameter 450 such that the first diameter 450 increases due to the rotation.

The second fluid 406 has a lower density than the first fluid 404. In some embodiments, the second fluid 406 is a gas, such as air. The second fluid 406 forms a bubble 424 within the first fluid 404 having a second diameter 454. An increase in the first diameter 450 increases a capacity of the cavity 410, such that the second diameter 454 is based on the first diameter 450 of the microfluidic cavity 410. In other words, the second diameter 454 of the bubble 424 is configured to increase as the first diameter 450 of the microfluidic cavity 410 increases due to rotation about the rotation axis 452.

The electrode arrangement 408 includes a pair 414 of electrodes 416 and 418 disposed on opposite sides of the microfluidic cavity 410 and are configured to interact through the microfluidic cavity 410. The second fluid 406 has a higher dielectric permittivity than the first fluid 404. As a result, a capacitance measured across the electrode pair 414 increases with an increase in the second diameter 454. Thus, the capacitance measured across the electrode pair 414 is indicative of the rotation rate of the microfluidic structure 402 about the rotation axis 452. The measuring device 409 is configured to determine the second diameter of the bubble 424 based on the capacitance measured across the electrode pair 414, and to determine the rotation rate of the microfluidic structure 402 based on the determined second diameter 454.

Figure 4:
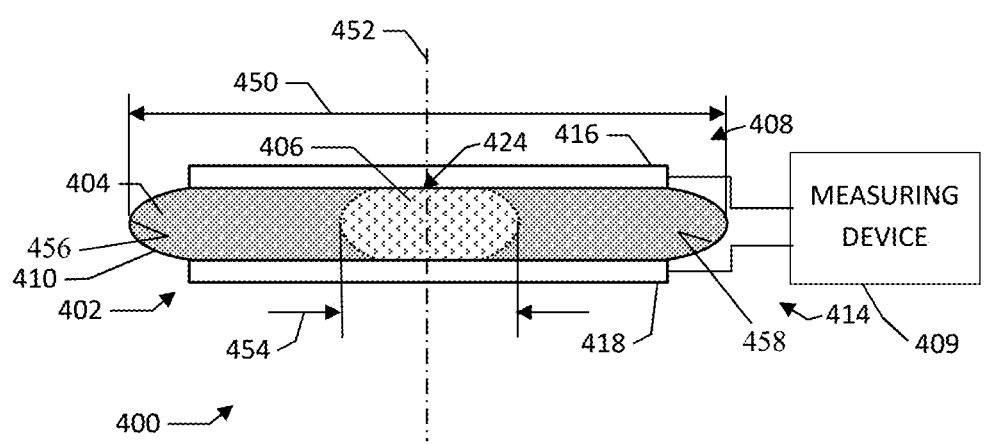
FIG. 4 is a side plan view of the sensor from FIG. 3 subject to a nonzero rotation rate.

In FIG. 3, the rotation rate of the microfluidic structure 402 is zero. FIG. 4 depicts the microfluidic structure 402 with a nonzero rotation rate about the rotation axis 452. Due to the higher density of the first fluid 404 relative to the second fluid 406, the first fluid 404 has a higher inertia relative to the second fluid 406. As a result, the rotation of the microfluidic structure 402 about the rotation axis 452 biases the first fluid 404 away from the rotation axis 452 and pushes the first fluid 404 against inner sidewalls 456 and 458 of the microfluidic cavity 410 that are at least substantially perpendicular to the first diameter 450. A force of the first fluid 404 against the inner sidewalls 456 and 458 causes the microfluidic structure 402 to flex and increases the first diameter 450 of the microfluidic cavity 410 in FIG. 4 relative to the diameter depicted in FIG. 3. Since the second diameter 454 of the second fluid 406 is based on the first diameter 450, the second diameter 454 in the rotating microfluidic structure 402 in FIG. 4 is larger than the diameter depicted in FIG. 3.

In another embodiment of a flexible microfluidic sensor according to this disclosure, the sensor has a structure similar to the sensor 400 depicted in FIGS. 3 and 4, and the resistance of the first fluid 404 is higher than the resistance of the second fluid 406. Due to the difference in resistances, an increase in the second diameter 454 of the bubble 424 of the second fluid 406 decreases a total resistance across the electrodes 416 and 418. The measuring device 409, in this embodiment, is configured to determine second diameter 454 of the bubble 424 based on the resistance measured across the electrode pair 414, and to determine the rotation rate of the microfluidic structure 402 based on the determined resistance.

While the embodiments depicted in FIGS. 1-4 and described above disclose using particular physical and electrical properties, other embodiments use other properties or combinations of properties. Further, in some embodiments, the first fluid has multiple different physical or electronic properties from the second fluid that are used to determine the physical condition of a microfluidic structure. In one embodiment, a resistance measured across an electrode arrangement that persists beyond a predetermined period of time is used to determine a static orientation of a microfluidic structure, a change in total resistance across the electrode arrangement is used to determine an acceleration of the microfluidic structure, and a change in capacitance across the electrode arrangement is used to determine a rotation of the microfluidic structure.

Additionally, while the measurement devices 109, 209, and 409 in the embodiments above are included with the sensors 100, 200, and 400, in other embodiments, a measurement device is external to the sensor and is connected via electrical contacts.

As noted above, each of a reorientation, acceleration, and rotation of a microfluidic structure in the embodiments above affects the arrangement of the first and second fluids. In some instances, a similar arrangement of the fluids can result from different actions. For example, an acceleration along a first axis of a microfluidic structure can cause a bubble of the second fluid to move to a new first location, and a reorientation of the microfluidic structure can also cause the bubble to move to the same first location. Thus, given only a previous location and a new location of the bubble, it may be at least partially indeterminate whether the change in location resulted from a reorientation, an acceleration, or a rotation, or some combination thereof. As discussed below, it is possible to isolate orientation, acceleration, and rotation from each other via several different techniques.

In one embodiment, a microfluidic device according to this disclosure includes a first microfluidic sensor configured as a dedicated tilt sensor, and a second microfluidic sensor configured as at least one of an acceleration sensor and rotation sensor. A measuring device associated with the microfluidic device is configured to use the tilt sensor to determine a reference frame for the acceleration or rotation sensor, and thereby decouple the orientation of the microfluidic device from rotation and acceleration.

In another embodiment, a measurement device is configured to make a determination of at least one of orientation, acceleration, and rotation based on a set of successive values of an electrode arrangement taken over time. Specifically, a time period over which a microfluidic structure is subjected to an acceleration or rotation is generally short relative to a time period over which the microfluidic is maintained in a substantially static orientation. Thus, taking a set of successive values of an electrode arrangement over time, enables differentiating between relatively transient values associated with an acceleration and relatively static values associated with an orientation.

In a further embodiment, values of a set of different electrical properties are taken from an electrode arrangement. In one example, the capacitance of individual electrode pairs is used to determine a location of a bubble along a microfluidic channel indicative of acceleration or orientation, and a total capacitance of the entire electrode arrangement is used to determine a rotation rate. A measurement device is configured to use the rotation rate to define a reference frame for the microfluidic structure, and thereby decouple the rotation of the microfluidic device from acceleration and orientation.

In another embodiment, the actions of reorientation, acceleration, and rotation are decoupled by taking values of multiple different electrode arrangements that are respectively aligned with different axes, as discussed in more detail below.

Figure 5:
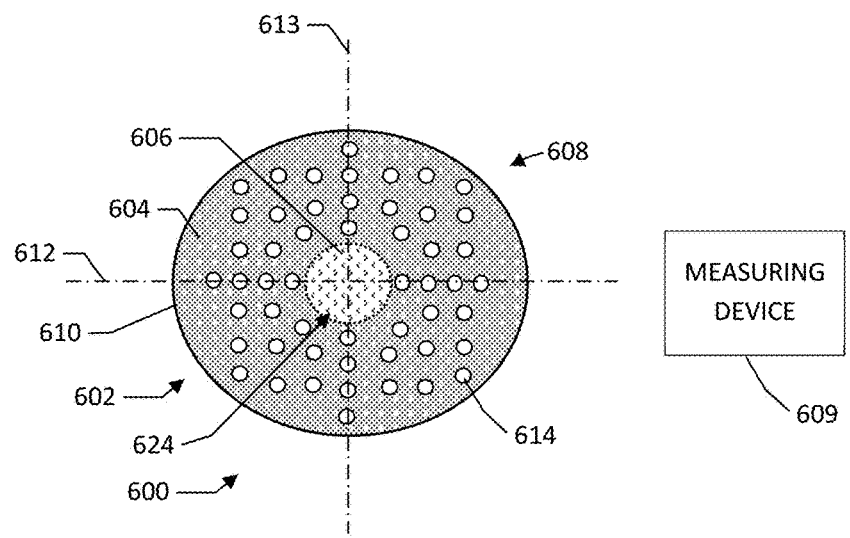
FIG. 5 is a top plan view of another exemplary embodiment of a flexible microfluidic sensor according to this disclosure.

FIG. 5 depicts a top schematic view of another exemplary embodiment of a flexible microfluidic sensor 600 according to this disclosure. The sensor 600 includes a flexible microfluidic structure 602, a first fluid 604 and second fluid 606 disposed within the microfluidic structure 602, an electrode arrangement 608, and a measurement device 609.

The microfluidic structure 602 defines a microfluidic chamber 610 which, in this embodiment includes a microfluidic cavity 610 that extends over both a first axis 612 and a second axis 613 perpendicular to the first axis 612. In this embodiment, the microfluidic cavity 610 has a substantially circular shape, but other shapes are also contemplated in other embodiments.

The electrode arrangement 608 includes a set of electrode pairs 614 that are distributed circumferentially and radially over the microfluidic cavity 610. For the sake of clarity, electric connections between the electrode pairs 614 and the measuring device 609 are omitted from FIG. 5.

In this embodiment, the second fluid 606 is less dense and less resistance than the first fluid 604, and forms a bubble 624 within the first fluid 604. A location of the bubble 624 along the first axis 612 is based on at least one of an acceleration of the microfluidic structure 602 along the first axis 612, and an orientation of the first axis 612 of the microfluidic structure 602 relative to a direction of gravity (into the page in FIG. 6). Similarly, the location of the bubble 624 along the second axis 613 is based on at least one of an acceleration of the microfluidic structure 602 along the second axis 613 and an orientation of the second axis 613 of the microfluidic structure 602 relative to a direction of gravity.

The electrode pairs 614 in the electrode arrangement 608 enable determining at least one of the orientation, acceleration, and rotation of the microfluidic structure 602 in a manner similar to the embodiments discussed above. Due to the difference in resistance between the first fluid 604 and second fluid 606, the resistance measured across each of the electrode pairs 614 is based on a relationship between the location of the bubble 624 and the electrode pairs 614. In other words, a resistance measured across an electrode pair 414 proximate to the bubble 624 is less than a resistance measured across an electrode not proximate to the bubble 624. Since the electrode pairs 614 are distributed across both the first axis 612 and the second axis 613, determining that the bubble 224 is proximate to a particular electrode pair 414 is indicative of a location of the bubble 624 along each of the first axis 612 and the second axis 613. The measurement device 609 is thus configured to determine a location of the bubble 624 along both the first axis 612 and the second axis 613 based on the resistances measured across the electrode pairs 614. Further, the measurement device 609 is configured to determine at least one of an acceleration of the microfluidic structure 602 along the first axis 612, and an orientation of the first axis 612 of the microfluidic structure 602 relative to a direction of gravity based on the location of the bubble 624 along the first axis 612, and to determine at least one of an acceleration of the microfluidic structure 602 along the second axis 613 and an orientation of the second axis 613 of the microfluidic structure 602 relative to a direction of gravity based on the location of the bubble 624 along the second axis 613.

Additionally, as noted above, in some embodiments, the measurement device is further configured to isolate determination of accelerations from determination of orientations by making multiple determinations over time, whereby transient locations of the bubble 624 are indicative of accelerations while static locations are indicative of orientations.

In another embodiment, rotation of the microfluidic structure 602 causes the microfluidic cavity 610 to flex outwards, increasing a diameter of the bubble 624 and thereby modifies a total capacitance of the electrode arrangement 608 that enables the measurement device 609 to determine the rotation of the microfluidic structure 602 about a rotation axis perpendicular to the first axis 612 and second axis 613.

Figure 6:
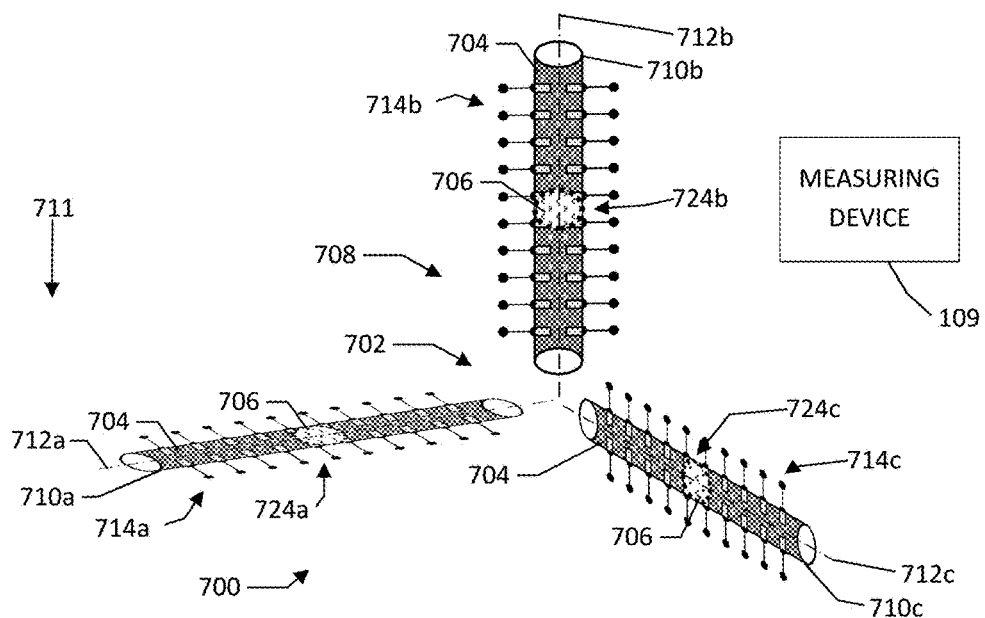
FIG. 6 is a perspective plan view of another exemplary embodiment of a flexible microfluidic sensor according to this disclosure.

FIG. 6 depicts a perspective schematic view of another exemplary embodiment of a flexible microfluidic sensor 700 according to this disclosure. The sensor 700 includes a flexible microfluidic structure 702, a first fluid 704 and second fluid 706 disposed within the microfluidic structure 702, an electrode arrangement 708, and a measurement device 709. For the sake of clarity, electric connections between the microfluidic structure 702 and the measuring device 709 are omitted in FIG. 7.

In this embodiment, the microfluidic structure 702 defines a microfluidic chamber that includes a first microfluidic channel 710a that extends along a first axis 712a, a second microfluidic channel 710b that extends along a second axis 712b perpendicular to the first axis 712a, and a third microfluidic channel 710c that extends along a third axis 712c perpendicular to both the first axis 712a and the second axis 712b. Each of the microfluidic channels 710a-c is closed off from each other, and is respectively filled with the first fluid 704 and a bubble 724a, 724b, and 724c respectively of the second fluid 706.

The electrode arrangement 708 includes first, second, and third sets of pairs 714a-c of electrodes that are respectively disposed along the first axis 712a, second axis 712b, and third axis 712c on opposing sides of the corresponding microfluidic channels 710a-c. Thus, the structure of each of the individual microfluidic channels 710a-c is similar to the structure of the microfluidic channel 110 depicted in FIG. 2a. The microfluidic channel 710a, electrode pairs 714a, and bubble 724a enable determining at least one of an orientation of the first axis 712a of the microfluidic structure 702 relative to gravity, an acceleration of the microfluidic structure 702 along the first axis 712a, a rotation of the microfluidic structure 702 about the second axis 712b, and a rotation about the third axis 712c. The microfluidic channel 710b, electrode pairs 714b, and bubble 724b enable determining at least one of an orientation of the second axis 712b of the microfluidic structure 702 relative to gravity, an acceleration of the microfluidic structure 702 along the second axis 712b, a rotation about the first axis 712a, and a rotation of the microfluidic structure 702 about the third axis 712c. The microfluidic channel 710c, electrode pairs 714c, and bubble 724c enable determining at least one of an orientation of the third axis 712c of the microfluidic structure 702 relative to gravity, an acceleration of the microfluidic structure 702 along the third axis 712c, a rotation of the microfluidic structure 702 about the first axis 712a and a rotation about the second axis 712b.

In some embodiments, the measurement device 709 is configured to use determinations of at least one of orientation, acceleration, and rotation relative to multiple axes in order to improve an accuracy of at least one other determination. For example, motion of the bubble 724a along the first axis 712a can result from an acceleration along the first axis 712a, a rotation about the second axis 712b, a rotation about the third axis 712c, or a combination thereof. In one embodiment, the measurement device 709 is configured to use a determination of a rotation of the microfluidic structure 702 about the second axis 712b based on the microfluidic channel 710c, electrode pairs 714c, and bubble 724c to isolate a determination of an acceleration along the first axis 712a based on the microfluidic channel 710a, electrode pairs 714a, and bubble 724a from a determination of a rotation about the second axis 712b based on the microfluidic channel 710a, electrode pairs 714a, and bubble 724a.

Figure 7:
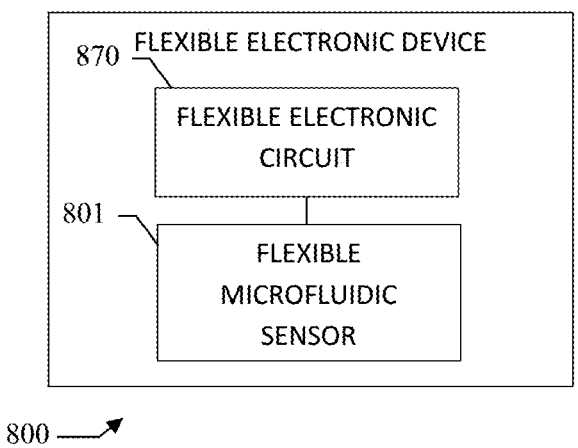
FIG. 7 is a functional block diagram of an exemplary embodiment of a flexible electronic device according to this disclosure.

FIG. 7 is a functional block diagram of an exemplary embodiment of a flexible electronic device 800 according to this disclosure. The device 800 includes at least one flexible electronic circuit 870 and a flexible microfluidic sensor 801.

In conventional flexible electronic devices, inertial sensors for sensing orientation, acceleration, and rotation are generally formed on silicon platforms in conformance with mass manufacturing processes inherited from the semiconductor industry. While silicon-based sensors are generally fast-acting and highly accurate, the silicon base results in a heterogeneous integration with the more flexible material of a flexible circuit. The more rigid silicon not only can create bending creases and stress points that can lead to damage of the device, but can also decrease the overall flexibility of the device.

In comparison, the flexibility of the sensor 802 enables homogeneous integration of the sensor 801 with the flexible circuit 807. In one embodiment, the flexible circuit 870 includes a circuit printed on or encased in a flexible polymer, and the sensor 801 includes a microfluidic structure formed with the flexible polymer.

The rearrangement of fluids due to a reorientation, acceleration, or rotation is generally slow relative to the highly responsive electromechanical interactions used by silicon-based micro-electromechanical (MEMS) devices. As a result, a sensor according to this disclosure may be less rapidly responsive than a conventional silicon-based inertial sensor. Further, fluid-based determinations may be less accurate than the highly precise measurements made possible by extremely sensitive silicon-based sensors. However, many applications for flexible electronic devices are more limited by the flexibility of the device than by the precision or rapidity of the measurements.

For example, many applications for flexible electronic devices include responding to human motion. Human motion generally occurs on a time scale far slower than the typical response time of a silicon-based sensor. Further, in many applications, high precision in sensor results is unnecessary.

Figure 8:
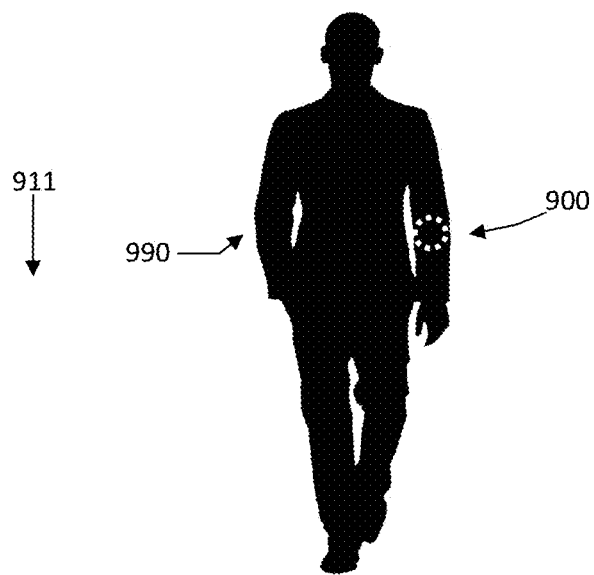
FIG. 8 is an illustration of an exemplary embodiment of a flexible electronic device according to this disclosure in use on a wrist of a user.

FIG. 8 depicts another exemplary embodiment of a flexible electronic device 900 according to this disclosure. The device 900 has a microfluidic sensor, such as one of the embodiments of a sensor discussed above. The sensor is configured to sense an acceleration of at least a portion of a user 990 in the direction of gravity 911. The device 900 further has a flexible electronic circuit configured to determine that the sensed acceleration indicates that the user has taken a step, and count a total of steps taken by the user.

In various embodiments, flexible electronic devices are used for a wide variety of applications. In one embodiment, an electronic device is configured to determine that at least one rotation, acceleration, and orientation corresponds to a specific motion of a user. For example, in one embodiment, a flexible electronic device according to this disclosure is integrated into a flexible wristband, and is configured to determine that a user is, for example, swinging a tennis racket or golf club, throwing a ball, or the like.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the disclosure.

The invention claimed is:

1. A flexible microfluidic sensor, comprising:
a flexible microfluidic structure that defines at least one microfluidic chamber;
a first material and a second material disposed in the at least one chamber, the second material having at least one physical property that is different than a physical property of the first material, and the second material having at least one electronic property that is different than an electronic property of the first material; and
an electrode arrangement including at least one pair of electrodes that are spaced apart from each other with at least a portion of the at least one chamber located functionally directly between the electrodes such that at least one electronic property measured across the at least one pair of electrodes is based on a relationship between the second material and the at least one pair of electrodes;
wherein the relationship between the second material and the at least one pair of electrodes is based on a physical condition of the microfluidic structure.

2. The sensor of claim 1, wherein:
the physical condition of the microfluidic structure includes at least one of the group consisting of an orientation of the microfluidic structure, an acceleration of the microfluidic structure, and a rotation rate of the microfluidic structure.

3. The sensor of claim 1, wherein:
the first material is a first fluid; and
the second material is a second fluid, a solid, or a solid shell that includes a second fluid.

4. The sensor of claim 1, wherein the at least one physical property includes at least one of the group consisting of density and viscosity.

5. The sensor of claim 4, wherein the at least one electrical property measured across the at least one pair of electrodes includes at least one of the group consisting of resistance and capacitance.

6. The sensor of claim 1, wherein:
the at least one chamber includes a first microfluidic channel that extends along a first axis;
the first material is a first fluid;
the second material is a second fluid forms a first bubble within the first fluid in the first microfluidic channel;
the at least one pair of electrodes includes a first set of electrode pairs distributed along the first axis of the first microfluidic channel such that at least one electronic property measured across the first set of electrode pairs is based on a relationship between the first bubble and the first set of electrode pairs; and
the relationship between the first bubble and the first set of electrode pairs is based on at least one of the group consisting of an orientation of the first axis relative to a direction of gravity, an acceleration of the microfluidic structure along the first axis, and a rotation of the microfluidic structure perpendicular to the first axis.

7. The sensor of claim 6, wherein the relationship between the first bubble and the first set of electrode pairs includes at least one of the group consisting of a location of the first bubble along the first axis and a diameter of the first bubble.

8. The sensor of claim 7, wherein each electrode in the first set of electrode pairs includes a respective electrical contact.

9. The sensor of claim 8, further comprising:
a measurement device electrically connected to the electrical contacts of the electrodes in the first set of electrode pairs, the measurement device configured to:
determine the relationship between the first bubble and the first set of electrode pairs based on the at least one electrical property measured across the first set of electrode pairs distributed along the first axis; and
determine, based on the determined relationship, a physical condition of the microfluidic structure.

10. The sensor of claim 9, wherein:
each electrode pair in the first set of electrode pairs has a respective resistive load so that the resistive load of the first set of electrode pairs varies along the first axis;

the at least one electrical property measured across the first set of electrode pairs includes resistance, such that a total resistance of the first set of electrode pairs changes based on the location of the first bubble along the first microfluidic channel; and the measurement device is further configured to determine the location of the first bubble along the first microfluidic channel based on the total resistance of the first set of electrode pairs.

11. The sensor of claim 7, wherein:

the at least one chamber further includes a second microfluidic channel that extends along a second axis extending perpendicularly to the first axis;

the second fluid forms a second bubble within the first fluid in the second microfluidic channel;

the at least one pair of electrodes further includes a second set of electrode pairs distributed along the second axis of the second microfluidic channel such that at least one electronic property measured across the second set of electrode pairs is based on a relationship between the second bubble and the second set of electrode pairs;

the relationship between the second bubble and the second set of electrode pairs is based on at least one of the group consisting of an orientation of the second axis relative to the direction of gravity, an acceleration of the microfluidic structure along the second axis, and a rotation of the microfluidic structure perpendicular to the second axis.

12. The sensor of claim 11, wherein:

the at least one chamber further includes a third microfluidic channel that extends along a third axis extending perpendicularly to the first axis and perpendicularly to the second axis;

the second fluid forms a third bubble within the first fluid in the third microfluidic channel;

the at least one pair of electrodes further includes a third set of electrode pairs distributed along the third axis of the second microfluidic channel such that at least one electronic property measured across the third set of electrode pairs is based on a relationship between the third bubble and the third set of electrode pairs;

the relationship between the third bubble and the third set of electrode pairs is based on at least one of the group consisting of an orientation of the third axis relative to the direction of gravity, an acceleration of the microfluidic structure along the third axis, and a rotation of the microfluidic structure perpendicular to the third axis.

13. The sensor of claim 1, wherein:

the at least one chamber includes a microfluidic cavity that extends along a first axis and along a second axis perpendicular to the first axis:

the first material is a first fluid;

the second material is a second fluid that forms a bubble within the first fluid in the microfluidic cavity;

the at least one electronic property measured across the at least one pair of electrodes is based on a relationship between the bubble and the at least one pair of electrodes; and the physical condition of the microfluidic structure includes at least one of the group consisting of:
an acceleration of the microfluidic structure along the first axis;
an acceleration of the microfluidic structure along the second axis;
an orientation of the second axis relative to a direction of gravity;
an orientation of the first axis relative to the direction of gravity; and
a rotation of the microfluidic structure about a third axis perpendicular to the first axis and the second axis.

14. The sensor of claim 1, wherein the microfluidic structure consists of flexible polymer material.

15. The sensor of claim 14, wherein the flexible polymer material includes at least one of the group consisting of poly-dimethyle-siloxane and poly(p-xylylene).

16. A flexible microfluidic sensor, comprising:

a flexible microfluidic structure that defines at least one microfluidic chamber;

a first material and a second material disposed in the at least one chamber, the second material having at least one physical property that is different than a physical property of the first material, and the second material having at least one electronic property that is different than an electronic property of the first material; and an electrode arrangement including at least one pair of electrodes that are spaced apart from each other with at least a portion of the at least one chamber located functionally directly between the electrodes such that at least one electronic property measured across the at least one pair of electrodes is based on a relationship between the second material and the at least one pair of electrodes;

wherein:
the relationship between the second material and the at least one pair of electrodes is based on a physical condition of the microfluidic structure;
the at least one chamber includes a microfluidic cavity that extends along a first axis and along a second axis perpendicular to the first axis:
the first material is a first fluid;
the second material is a second fluid that forms a bubble within the first fluid in the microfluidic cavity;
the at least one electronic property measured across the at least one pair of electrodes is based on a relationship between the bubble and the at least one pair of electrodes; and
the physical condition of the microfluidic structure includes at least one of the group consisting of:
an acceleration of the microfluidic structure along the first axis;
an acceleration of the microfluidic structure along the second axis;
an orientation of the second axis relative to a direction of gravity;
an orientation of the first axis relative to the direction of gravity; and
a rotation of the microfluidic structure about a third axis perpendicular to the first axis and the second axis;
the microfluidic cavity has a first diameter, and is configured to flex due to rotation of the microfluidic structure about the third axis such that the first diameter increases; and
the bubble has a second diameter that is based on the first diameter, such that the second diameter is based on the rotation of the microfluidic structure about the third axis.

17. The sensor of claim 16, wherein:

the at least one electronic property measured across the at least one pair of electrodes includes capacitance; and the at least one electronic property of the second fluid includes dielectric permittivity such that the capacitance measured across at least one electrode pair changes based on the second diameter of the at least one bubble.

18. The sensor of claim 17, further comprising:
a measurement device electrically connected to the at least one electrode pair and configured to determine the rotation rate of the microfluidic structure based on the capacitance measured across the at least one electrode pair.

19. A flexible electronic device, comprising:
at least one flexible electronic circuit; and
a flexible microfluidic sensor homogeneously integrated with the at least one flexible electronic circuit, the flexible microfluidic sensor including:
a flexible microfluidic structure that defines at least one microfluidic chamber;
a first material and a second material disposed in the at least one chamber, the second material having at least one physical property that is different than a physical property of the first material, the second material having at least one electronic property that is different than an electronic property of the first material, and at least one of the group consisting of the first material and the second material being a fluid; and
an electrode arrangement including at least one pair of electrodes that are spaced apart from each other with at least a portion of the at least one chamber located functionally directly between the electrodes such that at least one electronic property measured across the at least one pair of electrodes is based on a relationship between the second material and the at least one pair of electrodes;
wherein the relationship between the second material and the at least one pair of electrodes is based on a physical condition of the microfluidic structure.

20. The device of claim 19, wherein the physical condition of the microfluidic structure is indicative of at least one of the group consisting of an orientation, an acceleration, and a rotation rate of at least a portion of a human user.

* * * * *